United States Patent [19]
Becker

[11] Patent Number: 6,019,102
[45] Date of Patent: Feb. 1, 2000

[54] DRAPE FOR MULTIPLE-TIERED STERILE HOSPITAL SURFACE AND ASSOCIATE METHODS

[76] Inventor: Dan L. Becker, 12153 Gray Birch Cir., Orlando, Fla. 32832

[21] Appl. No.: 09/160,812

[22] Filed: Sep. 25, 1998

[51] Int. Cl.[7] .................................................. A61B 19/00
[52] U.S. Cl. .......................................... 128/849; 128/855
[58] Field of Search ..................... 128/849–856

[56] References Cited

U.S. PATENT DOCUMENTS

| | | | |
|---|---|---|---|
| 4,873,997 | 10/1989 | Marshall | 128/849 |
| 5,151,314 | 9/1992 | Brown | 128/849 |
| 5,170,804 | 12/1992 | Glassman . | |
| 5,411,036 | 5/1995 | Wilks | 128/849 |
| 5,560,974 | 10/1996 | Langley | 128/849 |
| 5,592,952 | 1/1997 | Bohn | 128/849 |
| 5,766,737 | 6/1998 | Willey | 128/849 |

OTHER PUBLICATIONS

Sales Express, Inc., Table–Table Instructions, Brochure.
Sales Express, Inc., Table–Table the O.R. Backtable Organizer, Brochure.
Blickman Tables . . . the long–term investment!, Brochure.

*Primary Examiner*—Michael A. Brown
*Attorney, Agent, or Firm*—David G. Maire; Holland & Knight, LLP

[57] ABSTRACT

A sterile surgical drape is adapted to cover the surfaces of a multiple-tiered table such as is typically used for holding surgical instruments. Those drape sections (300,400) for covering surfaces above the bottom surface (200) are fitted so as to avoid impeding access to and visibility of those surfaces immediately beneath. Clear sections (300) of the drape are provided to extend between tiers for improved visualization from behind the table. Cuffs in the flap top section of the drape (410) are also provided for aiding handling and draping of surgical table by hospital personnel. Hook-and-loop fasteners (310) on the back of the clear middle section (300) are provided to be mated to hook-and-loop fasteners (312) on the under portion of the instrument table.

30 Claims, 2 Drawing Sheets

DRAPE FOR MULTIPLE-TIERED STERILE HOSPITAL SURFACE AND ASSOCIATE METHODS

BACKGROUND OF THE INVENTION

1. Field of the Invention

The present invention relates to sterile surface covers, and, more particularly, to drapes for instrument tables in operating rooms.

2. Description of Related Art

In hospital operating rooms, areas that are sterile and nonsterile are carefully delineated. Typically a surface that is to hold instruments, such as a metal table, is covered by a sterile drape such as are known in the art. The surface of the table itself is considered nonsterile, being made sterile by the application of a drape. Any area below the draped surface is also considered nonsterile.

Fitted drapes are known for use on Mayo stands, which are supported along one edge of the table surface. Conventional drapes are also known for covering a single-tiered table surface.

SUMMARY OF THE INVENTION

It is an object of the present invention to provide a sterile drape for covering a two-tiered instrument table for use in an operating room.

It is another object to provide a method for covering a two-tiered table in an operating room.

It is a further object to provide a method or making a sterile drape for covering a two-tiered instrument table for use in an operating room.

It is an additional object to provide a method for making such a drape in a one-piece embodiment.

It is yet another object to provide a method for making such a drape in a two-piece embodiment.

These and other objects are achieved by the surgical drape and methods of the present invention. The surgical drape is adapted to cover the surfaces of a multiple-tiered instrument table such as is typically used for holding surgical instruments. Those drape sections for covering surfaces above the bottom surface are fitted so as to avoid impeding access to and visibility of those surfaces immediately beneath. Clear sections of the drape are provided to extend between tiers for improved visualization of the instruments from behind the table. Cuffs are also provided for aiding handling by a sterile nurse.

A method for making a surgical drape for covering instrument multiple-tiered surfaces comprises the steps of affixing a bottom drape portion to a bottom edge of a clear middle section of flexible material, the clear middle section affixed adjacent a rear edge of the bottom drape portion. A top edge of the clear middle section is affixed adjacent a front edge of an upper drape portion. Both side edges of the clear middle section are affixed to the corresponding side edges of the upper drape portion at a location in spaced relation from the front edge commensurate with the width of the surface to be covered. Thus the upper portion of the clear middle section forms a cover for the underneath portion of the top tier. The upper portion of the clear middle section is affixed to the undersection of the top tier of the instrument table by hook-and-loop fasteners. From the side affixing locations the clear section is free to extend between the bottom and upper tier and permits visualization of the bottom tier from behind the table while inhibiting contamination by nonsterile personnel positioned there.

It will be apparent to one skilled in the art that additional steps similar to those recited above can be employed to cover an instrument table having further surfaces. It will also be apparent that, although this particular embodiment is intended for use with tables having upper surfaces supported from the rear, alternate drape designs would be encompassed by the present invention for other instrument table types, and limitations are not intended for this particular table.

A method of using such a surgical drape comprises the steps of arraying the bottom drape section on the bottom table surface desired to be covered, with the clear section facing toward the rear. Next the upper drape section is lifted up, which also brings the upper portion of the clear section upward. The top portion of the clear middle section is positioned under the top tier of the instrument table, and the remaining portion of the clear section is arrayed along the rear of the table for permitting visualization.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

REFERENCE NUMERALS IN DRAWINGS

10—two-tiered instrument table
12—bottom tier of instrument table
14—top tier of instrument table
16—table's left support post for top tier
18—table's right support post for top tier
100—one piece embodiment of entire drape for multiple-tiered sterile hospital surfaces
200—entire bottom piece of drape
202—bottom piece of drape that conforms to instrument table bottom tier
204—front part of bottom section of drape that creates a bottom skirt hanging over the bottom front edge of instrument table
206—left side of bottom section of drape that hangs over left side of instrument table
208—right side of bottom section of drape that hangs over left side of instrument table
212—rear edge of bottom section of drape which falls over the back edge of the instrument table forming a protective skirt.
214—bottom section of drape in front of the cutouts for the table supports where the bottom portion of the drape is affixed to the clear middle section.
216—cutout in rear edge of bottom section of drape to accommodate left top tier table support
218—cutout in rear edge of bottom section of drape to accommodate right top tier table support
300—clear middle section of drape
302—top edge of clear middle section of drape 304—bottom edge of clear middle section of drape
306—left side of clear middle section of drape
308—right side of clear middle section of drape
310—hook-and-loop fastener attached to clear middle section of drape
312—hook-and-loop fastener attached to undersection of top tier of instrument table
400—entire top piece of drape
402—front edge of drape in the top tier section
404—the portion of top section of drape that overhangs back of instrument table
406—left side of top section of drape
408—right side of top section of drape
410—cuffed flap areas on top section of drape used for applying drape to instrument table

SUMMARY

In accordance with the present invention a sterile drape for a multiple-tiered hospital instrument table is comprised of a generally rectangular bottom sheet affixed to a clear middle sheet which is affixed to a generally rectangular top sheet and the means for continuous joining of said bottom, middle, and top sheet in a one piece embodiment and the means for applying said drape to a hospital instrument table.

DETAILED DESCRIPTION OF THE PREFERRED EMBODIMENTS

Figure 1:
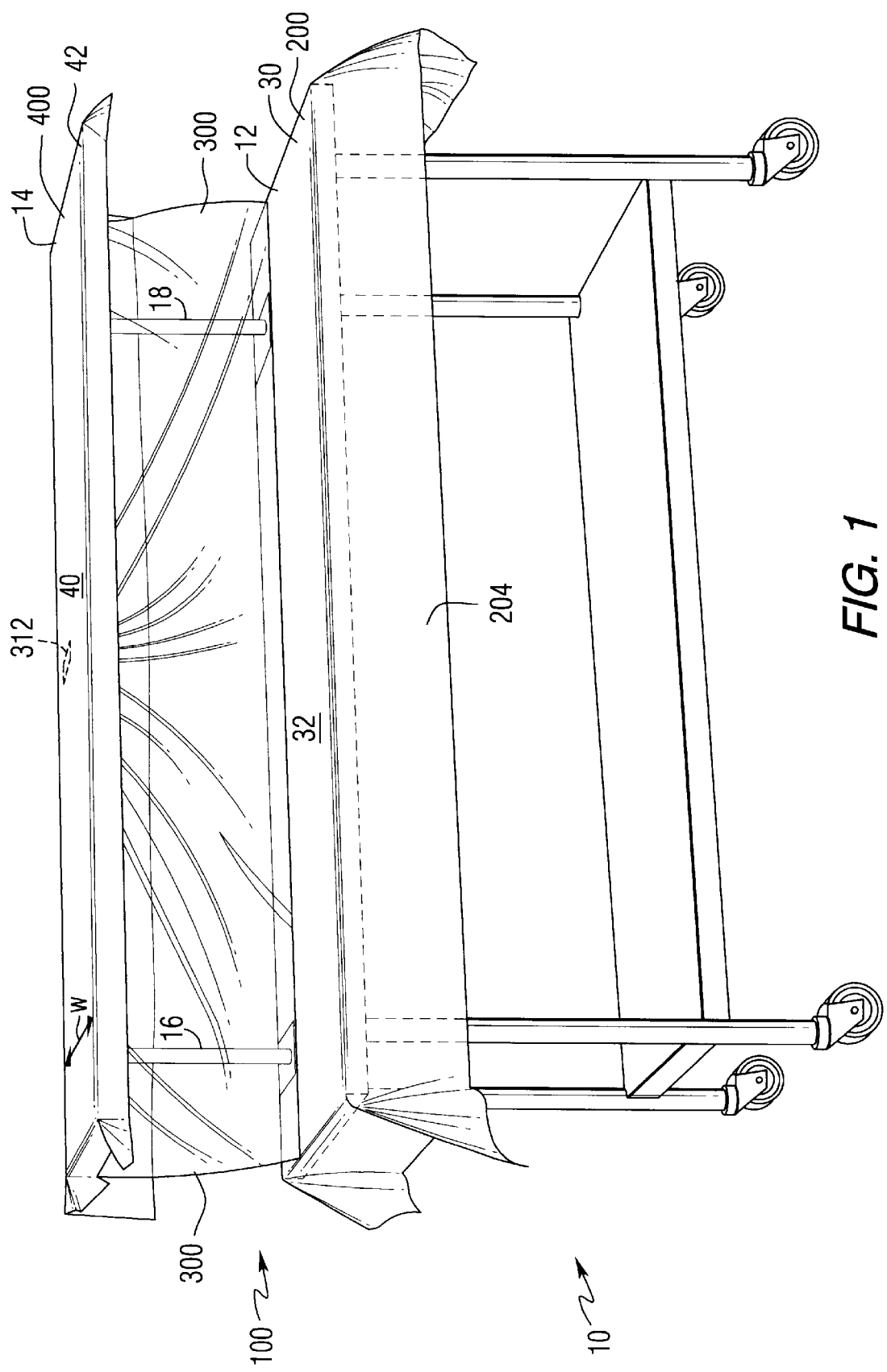
FIG. 1 is a perspective view of a surgical instrument table covered with the surgical sterile drape.
Figure 2:
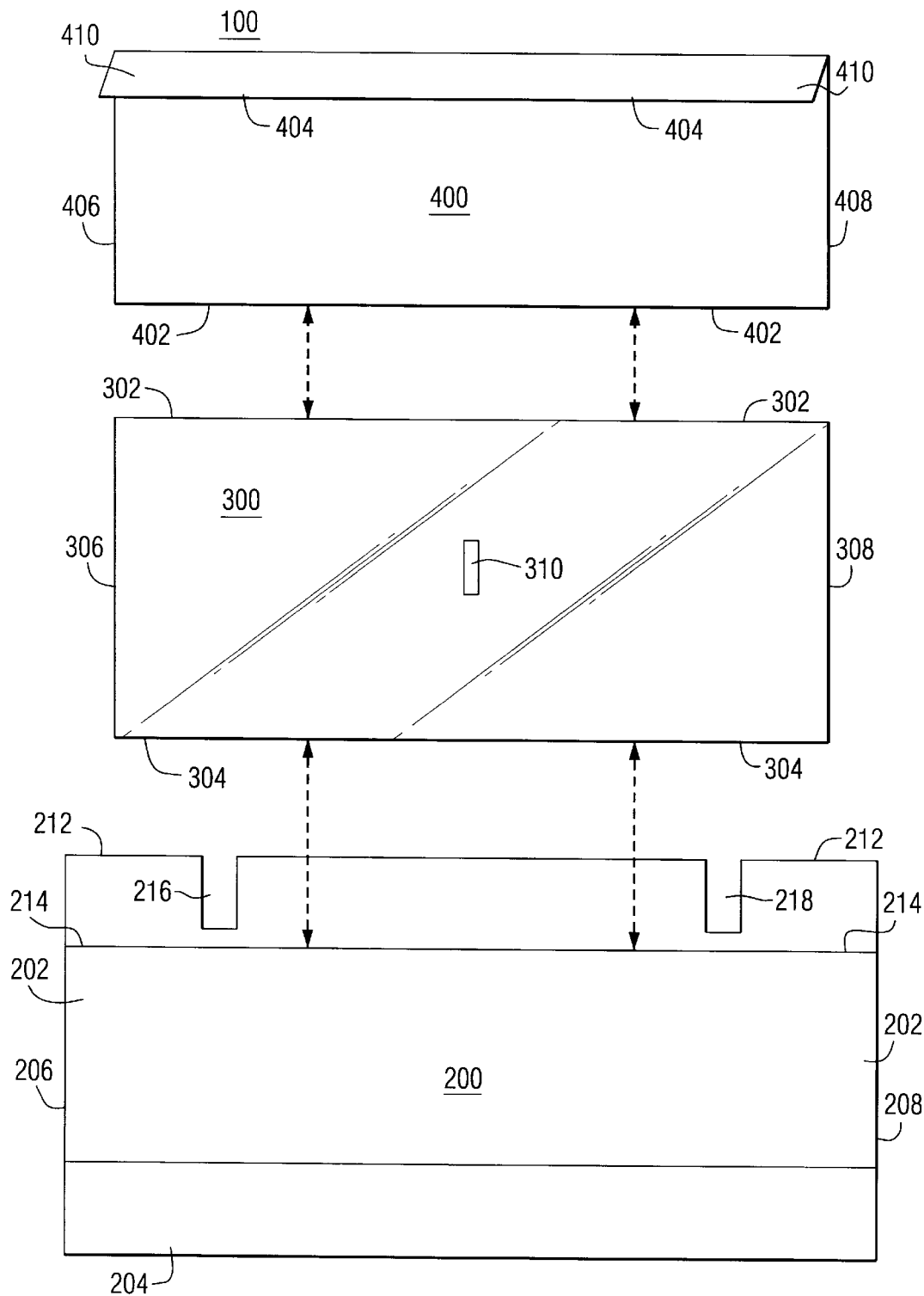
FIG. 2 is an exploded view of the one-piece embodiment of the surgical drape showing the attachment points of the three sections.

A description of the preferred embodiments of the present invention will now be presented with reference to FIGS. 1 and 2.

In a preferred embodiment the drape is for covering what is known in the art as a surgical "back instrument table", which will be shown as a table 10 having a bottom tier 12 and an upper tier 14, the two tiers 12, 14 connected by two rear posts 16, 18. The drape 100 is shown in place in FIG. 1 covering such a table 10.

Two embodiments of the present invention are provided: a one piece 100 and a two piece drape. The drape 100 is shown in exploded view in FIG. 2.

The bottom section 200 comprises a generally rectangular sheet of liquid-impervious material such as are known for use in the art. The liquid-impervious nature is important to prevent any spillage or leakage from seeping through the sheet, contacting the nonsterile, instrument table surface, and wicking back up through the sheet, which then would be contaminated. The bottom section 200 has a top surface 30 operable to cover the bottom tier 12 of the table 10 to define a sterile lower tier surface 32. In a particular embodiment the material comprises a plastic such as polyethylene, typically colored blue for this application, although this is not intended to be limiting. The sheet has a pair of cutouts 216,218 positioned along the rear edge 212 for admitting the table posts 16,18. The rear part of the material surrounding the cutouts 216,218 when in position on a table falls below the bottom tier 12 surface. The width and depth of the bottom section 200 are dimensioned for side and front draping along the side 206,208 and front edges 204, respectively.

Affixed atop the bottom section 200 is another rectangular piece of flexible material, bonded to the bottom section 200 to form a laminate. This surface section 202 is dimensioned generally to conform to the top of the bottom tier 12, is made of a cloth-like material such as a non woven fabric having a wood pulp base (e.g., Dexter®, made by DuPont).

A top section 400 also comprises a generally rectangular sheet of liquid-impervious material, for example, polyethylene, again typically colored blue. The top section 400 is also laminated with a non woven cloth-like material such as Dexter®. The rear edge 404 is turned upward and affixed along the sides to form a top flap 410, which serves as a cuff for assisting in placing the drape, as will be described in the following. Upper tier 14 has an upper tier surface (hidden by drape 100 in FIG. 1) and an opposed underside surface (hidden in FIG. 1). As illustrated in FIG. 1, the upper tier 14 and its underside surface are disposed at least partially above over the bottom tier 12. The upper tier surface is covered by top section 400 to define a sterile upper tier surface 40. Top section 400 also has a front edge 42.

A clear section 300 is affixed along its bottom edge 304 adjacent the bottom section's back edge 214 just forward of the cutouts 216,218. Clear section 300 is also affixed along its top edge 302 to the top section's front edge 402, and its side edges 306,308 are affixed to the corresponding side edges 406,408 of the upper drape portion 400 commensurate with the width W of the upper tier 14 (shown as darkened strips on FIG.2). Thus the upper portion 302 of the clear section 300 forms a flap for fitting to an upper tier 14 by tucking thereunder.

Preferably the clear section 300 is also made of a liquid-impervious material, such as, but not limited to, polyethylene, which has sufficient translucence to permit visualization of table surface there through.

In order to secure the flap onto the upper tier 14, further affixing means are also provided. In a preferred embodiment a piece 310 of one part of a hook-and-loop type fastener (Velcro®) is affixed to a back side of the clear section 300 generally in line with the inward ends of the side-affixing locations. This piece is for mating with a corresponding piece 312 affixed beneath and generally adjacent the rear edge of the top tier 14. When mated, the fastener pieces hold the central part of the clear section up and out of the way of the bottom tier 12.

The drape can be made in a two-piece embodiment, wherein the bottom section 200 and the clear section 300 are not affixed together, but merely abut each other; otherwise, the sections are constructed substantially the same as for the drape 100, with the clear section being longer to permit a draping behind the bottom tier 12.

The drape 100 as described above is made by forming the three sections 200,300,400 from the appropriate materials and affixing them together as shown in FIG. 2.

Operation

The drape 100 is used by removing it from a protective covering, placing it in the center of the bottom tier of the instrument table 12 and unfolding the drape 100 from the middle to each side of the table 12 so that the sterile side of the bottom section 200 is positioned upward. The exposed front part of the drape 204 is then brought forward to cover the front edge of the bottom tier 12. Moving to the rear of the table 10 the remaining exposed drape is brought back so that the cutouts 216,128 in the bottom section of drape 202 correspond to the posts 16,18 supporting the top tier 14. The drape will now have cuffed flap areas 410 exposed on both ends. The upper drape section 400 is then raised up by a person on either side of the instrument table 10 inserting hands into the flap areas 410, lifting the drape and placing upper drape section 400 on top tier of instrument table 14 with back overhang 404 draping over the rear portion of top tier of instrument table 14. Lifting the upper drape section 400 also brings the upper portion of the clear section 300 upward. To finish applying drape 100 middle section of drape 300 is affixed up and away from the bottom piece of drape 200 by means of hook-and-loop type fasteners 310, 312. The hook-and-loop fasteners on the back of the clear middle section 310 are joined to their corresponding mates 312 on the underside of the top tier of the instrument table 14, and the remaining portion of the clear section 300 is arrayed along the rear of the table.

It may be appreciated by one skilled in the art that additional embodiments may be contemplated, including additional drapes designed for surgical instrument tables having multiple tiers and supports thereof.

CONCLUSIONS, RAMIFICATIONS, AND SCOPE

Accordingly the reader will see that the sterile drape for the multiple-tiered hospital instrument table can be used to quickly and conveniently create a sterile field. Furthermore, the multiple-tiered drape has the additional advantages in that It permits the draping to be done by sterile or non-sterile personnel.

It allows for instrument trays to be seen on both levels as well as from the back of the table.

It provides a superior surface upon which multiple trays can be placed.

It provides a custom fit to the surface it is covering so as to keep the instrument trays in place.

Although the description above contains many specificities, these should not be construed as limiting the scope of the invention. Rather, as merely providing illustrations of the presently preferred embodiments of this invention currently in use in over fifty hospital operating rooms in the United States. Certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Thus the scope of the invention should be determined by the appended claims and their legal equivalents, rather than by the examples given.

I claim:

1. A drape for a table in an operating room, the table having a lower tier and an upper tier, the lower tier having a lower tier surface, the upper tier having an upper tier surface and an opposed underside surface disposed at least partially over the lower tier surface, the drape comprising:
   a bottom sheet having a top surface operable to cover the lower tier surface to define a sterile lower tier surface;
   a top sheet having a front edge and operable to cover the upper tier surface to define a sterile upper tier surface;
   a middle sheet having a bottom edge and a top edge, the bottom edge being attached to the top surface of the bottom sheet and the top edge being attached to the front edge of the top sheet for isolating the sterile lower tier surface from the underside surface.

2. The drape of claim 1, further comprising a side edge of the middle sheet being attached to a side edge of the top sheet to form a flap operable to fit over at least a portion of the upper tier.

3. The drape of claim 1, further comprising a means for holding a central portion of the middle sheet away from the sterile lower tier surface.

4. The drape of claim 1, further comprising a fastener attached to a back surface of the middle sheet.

5. The drape of claim 1, wherein the fastener comprises a hook and loop fastener.

6. The drape of claim 1, wherein the middle sheet comprises a clear material.

7. The drape of claim 1, further comprising a flap formed on a rear portion of the top sheet.

8. The drape of claim 1, wherein the table has a post between the upper tier and the lower tier, the drape further comprising a cutout formed in a rear portion of the bottom sheet and operable to fit around the post.

9. A drape for a table in an operating room, the table having a lower tier and an upper tier, the lower tier having a lower tier surface, the upper tier having an upper tier surface and an opposed underside surface disposed at least partially over the lower tier surface, the drape comprising:
   a first sheet having a top surface operable to cover the lower tier surface to define a sterile lower tier surface;
   a second sheet having a top section having a front edge and operable to cover the upper tier surface to define a sterile upper tier surface;
   the second sheet further having a middle section having a bottom edge and a top edge, the bottom edge abutting the top surface of the first sheet and the top edge being attached to the front edge of the top section for isolating the sterile lower tier surface from the underside surface.

10. The drape of claim 9, further comprising a side edge of the middle section being attached to a side edge of the top section to form a flap operable to fit over at least a portion of the upper tier.

11. The drape of claim 9, further comprising a means for holding a central portion of the middle section away from the sterile lower tier surface.

12. The drape of claim 9, further comprising a fastener attached to a back surface of the middle section.

13. The drape of claim 12, wherein the fastener comprises a hook and loop fastener.

14. The drape of claim 9, wherein the middle section comprises a clear material.

15. The drape of claim 9, further comprising a flap formed on a rear portion of the second sheet.

16. The drape of claim 9, wherein the table has a post between the upper tier and the lower tier, the drape further comprising a cutout formed in a rear portion of the first sheet and operable to fit around the post.

17. A draped table for an operating room, the draped table comprising:
   a table lower tier having a lower tier surface;
   a table upper tier having an upper tier surface and an opposed underside surface;
   a structure connecting the table lower tier and the table upper tier so that the underside surface is disposed at least partially above the table lower tier surface;
   a bottom sheet having a top surface disposed over the lower tier surface to define a sterile lower tier surface;
   a top sheet having a front edge and a top portion disposed over the upper tier surface to define a sterile upper tier surface;
   the top sheet further having a middle portion having a bottom edge and a top edge, the bottom edge abutting the top surface of the bottom sheet and the top edge being attached to the front edge of the top sheet for isolating the sterile lower tier surface from the underside surface.

18. The draped table of claim 17, wherein the bottom edge of the middle portion is attached to the top surface of the bottom sheet.

19. The draped table of claim 17, wherein the structure comprises a post connecting a rear portion of the upper tier and a rear portion of the lower tier, and further comprising a cut out in a rear portion of the bottom sheet for admitting the post, the post and the cutout being isolated from the sterile lower tier surface by the middle portion.

20. The draped table of claim 17, further comprising a side edge of the middle portion being attached to a side edge of the top portion to form a flap operable to fit over at least a portion of the upper tier.

21. The draped table of claim 17, further comprising a means for holding a central portion of the middle portion away from the sterile lower tier surface.

22. The draped table of claim 17, further comprising a fastener attached to a back surface of the middle portion.

23. The draped table of claim 22, wherein the fastener comprises a hook and loop fastener.

24. The draped table of claim 17, wherein the middle portion comprises a clear material.

25. The draped table of claim 17, further comprising a flap formed on a rear portion of the top sheet.

26. The draped table of claim 17, further comprising:

the structure further comprising a post connected between the upper tier and the lower tier; and a cutout formed in a rear portion of the bottom sheet operable to fit around the post.

27. A drape for a table in an operating room, the table having a lower tier and an upper tier, the lower tier having a lower tier surface, the upper tier having an upper tier surface and an opposed underside surface disposed at least partially over the lower tier surface, the drape comprising:

a bottom tier area operable to cover the lower tier surface to define a sterile lower tier surface;

a top tier area operable to cover the upper tier surface to define a sterile upper tier surface;

a middle area formed between a front portion of the top tier area and a rear portion of the bottom tier area and operable to isolate the sterile lower tier surface from the underside surface; and means for holding the middle area away from the sterile lower tier surface.

28. The drape of claim 27, wherein the means for holding further comprises a hook and loop fastener attached to the middle area.

29. The drape of claim 27, wherein the means for holding further comprises a fastener attached to the middle area.

30. The drape of claim 27, wherein the middle area comprises a clear portion.

* * * * *

UNITED STATES PATENT AND TRADEMARK OFFICE
CERTIFICATE OF CORRECTION

PATENT NO. : 6,019,102　　　　　　　　　　　　　　　　　　　　　　　　　Page 1 of 1
APPLICATION NO. : 09/160812
DATED : February 1, 2000
INVENTOR(S) : Dan L. Becker It is certified that error appears in the above-identified patent and that said Letters Patent is hereby corrected as shown below:

In the specification at Column 1, line 1, the following paragraph should be added at the beginning of the paragraph entitled "BACKGROUND OF THE INVENTION":

This application claims the benefit of U.S. Provisional Application No. 60/068,466, filed December 22, 1997.

Signed and Sealed this

Twenty-seventh Day of April, 2010

David J. Kappos
*Director of the United States Patent and Trademark Office*